United States Patent
Filla et al.

(10) Patent No.: US 6,696,439 B1
(45) Date of Patent: Feb. 24, 2004

(54) 5-HT$_{1F}$ AGONISTS

(75) Inventors: Sandra Ann Filla, Franklin, IN (US); Brian Michael Mathes, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/890,720

(22) PCT Filed: Feb. 11, 2000

(86) PCT No.: PCT/US00/02505

§ 371 (c)(1), (2), (4) Date: Aug. 1, 2001

(87) PCT Pub. No.: WO00/50426

PCT Pub. Date: Aug. 31, 2000

Related U.S. Application Data

(60) Provisional application No. 60/122,016, filed on Feb. 26, 1999.

(51) Int. Cl.⁷ .................... C07D 491/04; C07D 519/00; A61K 31/4355; A61P 25/06
(52) U.S. Cl. ................ 514/228.2; 514/233.8; 514/252.18; 514/302; 544/61; 544/127; 544/362; 546/115
(58) Field of Search ........... 514/228.12, 233.8, 514/252.18, 302; 544/61, 127, 362; 546/115

(56) References Cited

U.S. PATENT DOCUMENTS

| | | | |
|---|---|---|---|
| 5,714,495 A | | 2/1998 | Viaud et al. ............... 514/300 |
| 5,874,427 A | * | 2/1999 | Filla et al. ............... 514/214.01 |
| 6,001,849 A | * | 12/1999 | Elliott et al. ............... 514/300 |
| 6,133,290 A | * | 10/2000 | Krushinski et al. ......... 514/322 |
| 6,358,972 B1 | * | 3/2002 | Filla et al. .................. 514/300 |

FOREIGN PATENT DOCUMENTS

| | | |
|---|---|---|
| EP | 0 733 628 A | 9/1996 |
| EP | 0 737 685 A | 10/1996 |
| EP | 0 832 650 A3 A2 | 4/1998 |

OTHER PUBLICATIONS

Shiotani, Shunsaku; Tsuno, Masahiko; Tanaka, Noriyasu; Tsuiki, Miho; Itoh, Makoto, J. Heterocycl. Chem., 32(1), 129–39 (English) 1995.*

* cited by examiner

Primary Examiner—Mukund J. Shah
Assistant Examiner—Tom McKenzie

(74) Attorney, Agent, or Firm—R. Craig Tucker

(57) ABSTRACT

The present invention relates to substituted furo[3,2-b] pyridine compounds of formula I:

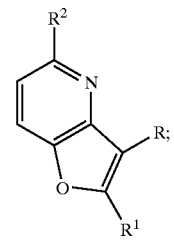

I or a pharmaceutical acid addition salt thereof; where;
R is

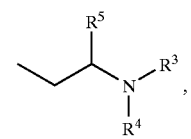

(a)

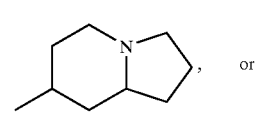

(b) or

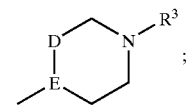

(c)

E—D is C=CH or CH—CH$_2$;
$R^1$ is hydrogen or $C_1$–$C_4$ alkyl;
$R^2$ is hydrogen, halo, hydroxy, —NR$^3$R$^4$, —SR$^3$, —C(O)R$^3$, —C(O)MR$^3$R$^4$, —NR$^3$SO$_2$R$^5$, —NHC(Q)NR$^3$R$^4$, —NHC(O)OR$^3$, or —NR$^3$C(O)R$^5$;
$R^3$, $R^4$, and $R^5$ are independently hydrogen, $C_1$–$C_4$ alkyl, $C_2$–$C_6$ alkenyl, $C_2$–$C_6$ alkynyl, or —(CH$_2$)$_n$aryl; or $R^3$ and $R^4$ combine, together with the nitrogen to which they are attached, form a pyrrolidine, piperidine, piperazine, 4-substituted piperazine, morpholine, or thiomorpholine ring;
n is 0, 1, 2, 3, 4, 5, or 6; and
Q is O or S.

The present invention further relates to pharmaceutical. formulations containing compounds formula I and to the use of compounds of formula I for activating 5-HT$_{1F}$ receptors, inhibiting neuronal protein extravasation, and treating and/or preventing migraine in a mammal.

18 Claims, No Drawings

5-HT$_{1F}$ AGONISTS

The present PCT national stage application claims priority to U.S. Provisional 60/122,016, filed Feb. 26, 1999.

Theories regarding the pathophysiology of migraine have been dominated since 1938 by the work of Graham and Wolff. *Arch. Neurol. Psychiatry*, 39:737–63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. Humphrey, et al., *Ann. NY Acad. Sci.*, 600:587–600, 1990. Recent work by Moskowitz has shown, however, that the occurrence of migraine headaches is independent of changes in vessel diameter. *Cephalalgia*, 12:5–7, 1992.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43 (suppl. 3):S16–S20 1993.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408–412, 1993. This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention relates to novel 5-HT$_{1F}$ agonists which inhibit peptide extravasation due to stimulation of the trigeminal ganglia, and are therefore useful for the treatment of migraine and associated disorders.

The present invention relates to a compound of formula I:

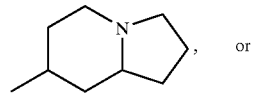

I and pharmaceutical acid addition salts thereof, where;

R is

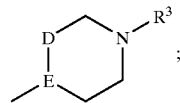

(a)

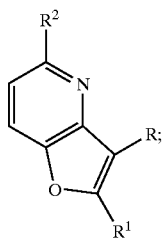

(b)

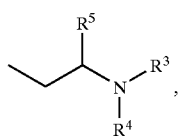

(c)

E—D is C=CH or CH—CH$_2$;
R$^1$ is hydrogen or C$_1$–C$_4$ alkyl;
R$^2$ is hydrogen, halo, hydroxy, —NR$^3$R$^4$, —SR$^3$, —C(O)R$^3$, —C(O)NR$^3$R$^4$, —NR$^3$SO$_2$R$^5$, —NHC(Q)NR$^3$R$^4$, —NHC(O)OR$^3$, or —NR$^3$C(O)R$^5$;
R$^3$, R$^4$, and R$^5$ are independently hydrogen, C$_1$–C$_4$ alkyl, C$_2$–C$_6$ alkenyl, C$_2$–C$_6$ alkynyl, or —(CH$_2$)$_n$aryl; or R$^3$ and R$^4$ combine, together with the nitrogen to which they are attached, form a pyrrolidine, piperidine, piperazine, 4-substituted piperazine, morpholine, or thiomorpholine ring;
n is 0, 1, 2, 3, 4, 5, or 6; and
Q is O or S.

This invention also relates to a pharmaceutical formulation comprising a compound of formula I, or a pharmaceutical acid addition salt thereof, and a pharmaceutical carrier, diluent, or excipient.

In addition, the present invention relates to a method for activating 5-HT$_{1F}$ receptors in mammals comprising administering to a mammal in need of such activation an effective amount of a compound of formula I, or a pharmaceutical acid addition salt thereof.

Moreover, the current invention relates to a method for inhibiting neuronal protein extravasation comprising administering to a mammal in need of such inhibition an effective amount of a compound of formula I, or a pharmaceutical acid addition salt thereof.

One embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of formula I.

The use of a compound of formula I for the activation of the 5-HT$_{1F}$ receptor, for the inhibition of peptide extravasation in general or due to stimulation of the trigeminal ganglia specifically, and for the treatment of any of the disorders described above, are all embodiments of the present invention.

The general chemical terms used throughout have their usual meanings. For example, the term "C$_1$–C$_4$ alkyd" refers to methyl, ethyl, n-propyl, isopropyl, n-butyl, isobutyl, sec-butyl, and tert-butyl. The term "C$_1$–C$_6$" alkyl includes those groups listed for C$_1$–C$_4$ alkyl and also refers to saturated, straight, or branched hydrocarbon chains of 5 to 6 carbon atoms. Such groups include, but are not limited to, pentyl, pant-2-yl, pent-3-yl, neopentyl, hexyl, and the like. The term "$C_3$–$C_8$ cycloalkyl" refers to cyclopropyl, cyclobutyl, cyclopentyl, cyclohexyl, cycloheptyl, and cyclooctyl.

The term "$C_2$–$C_6$ alkenyl" refers to mono-unsaturated straight or branched hydrocarbon chains containing from 2 to 6 carbon atoms and includes, but is not limited to, vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like.

The term "$C_2$–$C_6$ alkynyl" refers to straight or branched hydrocarbon chains containing 1 triple bond and from 2 to 6 carbon atoms and includes, but is not limited to, acetylenyl, propynyl, 2-butyn-4-yl, 1-butyn-4-yl, 1-pentyn-5-yl, 2-pentyn-5-yl and the like.

The terms "$C_1$–$C_6$ alkoxy" and "$C_1$–$C_4$ alkoxy" refer respectively to a $C_1$–$C_6$ alkyl and $C_1$–$C_4$ alkyl group bonded through an oxygen atom. The term "heteroaryloxy" refers to a heteroaryl or substituted heteroaryl group bonded through an oxygen atom. The term "aryloxy" refers to a phenyl or substituted phenyl group bonded through an oxygen atom. The term "$C_1$–$C_4$ acyl" refers to a formyl group or a $C_1$–$C_3$ alkyl group bonded through a carbonyl moiety. The term "$C_1$–$C_4$ alkoxycarbonyl" refers to a $C_1$–$C_4$ alkoxy group bonded through a carbonyl moiety.

The term "aryl" refers to an optionally substituted phenyl.

The term "aryl" refers to an optionally substituted phenyl or optionally substituted heterocyclic ring.

The term "heterocyclic" is taken to mean an unsaturated 5- or 6-membered ring containing from 1 to 3 heteroatoms selected from: nitrogen, oxygen and sulfur, said ring optionally being benzofused. Heterocyclic rings include furanyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused heterocyclic rings include isoquinolinyl, benzoxazolyl, benzthiazolyl, quinolinyl, benzofuranyl, benzothiophenyl, indolyl, and the like.

The terms "substituted phenyl" and "substituted heterocycle" are taken to mean that the cyclic moiety in either case is substituted once with halo, cyano, nitro, $C_1$–$C_4$ acyl, trifluoromethane, trifluoromethoxy, $C_1$–$C_4$ alkoxycarbonyl, $C_1$–$C_6$ alkoxy, or $C_1$–$C_4$ alkyl, or two to five substituents independently selected from the halo group.

The term "amino protecting group" as used in this specification refers to a substituents commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as "Greene".

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since the compounds of this invention are amines, they are basic in nature and accordingly react with any of a number of inorganic and organic acids to form pharmaceutical acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The term "effective amount" means an amount of a compound of formula I which is capable of activating 5-$HT_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

All enantiomers, diastereomers, and mixtures thereof, are included within the scope of the present invention. For example, the compounds of formula I where R is indolizidin-6-yl contain two chiral centers located in the bicyclic ring. One chiral center is located at the bridgehead carbon in the ring system, and the other is located in the CH group bonded to the 3-position of the indole ring. For the purposes of the present application, the numbering system for naming the substituents around the indole ring and the R, R and S, S enantiomers are illustrated below where $R^1$ and $R^2$ are as defined above.

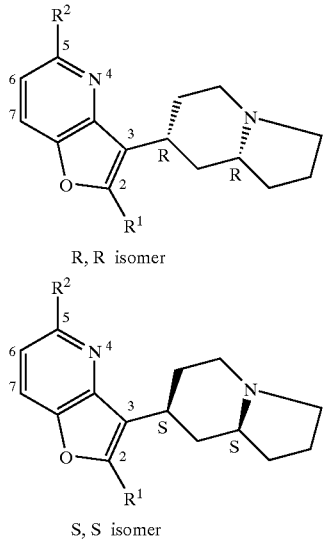

R, R isomer

S, S isomer

The following group is illustrative of compounds contemplated within the scope of this invention:

1) 2-methyl-3-(2-[N',N'-diethylamino]ethyl)-5-(4-propanesulfonylbenzamide)furo[3,2-b]pyridine hydrochloride;
2) 2-n-butyl-3-(2-[N'-methyl-N'-benzylamino]ethyl)-5-(4-fluorobenzamide)furo[3,2-b]pyridine;
3) 2-isobutyl-3-(2-[N'-methyl-N'-cyclopropylmethylamino]ethyl)-5-(4-iodobenzamide)furo[3,2-b]pyridine naphthalene-1-sulfonate;
4) 2-s-butyl-3-(2-[N'-methyl-N'-(2-[1-propylpyrazol-4-yl]ethyl)amino]ethyl)-5-(4-fluorobenzamide)furo[3,2-b]pyridine ditoluoyltartrate;
5) 2-methyl-3-(2-[N'-methyl-N'-s-butylaminoethyl)-5-isobutyramidefuro[3,2-b]pyridine;
6) 2-methyl-3-(2-[N'-methyl-N'-(2-[pyridin-4-yl]ethyl)amino]ethyl)-5-(4-fluorobenzamide)furo[3,2-b]pyridine malonate;
7) 2-methyl-3-(2-[N'-methyl-N'-(2-[1-isbpropylpyrazol-4-yl]ethyl)amino]ethyl)-5-butyramidefuro[3,2-b]pyridine mandelate;
8) 3-(2-[N'-methyl-N'-([4-bromothien-2-yl]methyl)amino]ethyl)-5-(4-fluorobenzamide)furo[3,2-b]pyridine hydrochloride;
9) 2-ethyl-3-(2-[N'-ethyl-N'-(2-[3-methylthiobenzofur-5-yl]ethyl)amino]ethyl)-5-(pyridine-2-carboxamide)furo[3,2-b]pyridine;
10) 2-propyl-3-(2-[N'-isopropyl-N'-(3-[isobenzofur-2-yl]propyl)amino]ethyl)-5-(4-fluorobenzamide)furo[3,2-b]pyridine;
11) 2-methyl-3-(2-[N'-butyl-N'-([pyrrol-3-yl]methyl)amino]ethyl)-5-(4-fluorobenzamide)furo[3,2-b]pyridine maleate;
12) 2-methyl-3-(2-[N'-methyl-N'-([5-cyanoimidazol-2-yl]methyl)amino]ethyl)-5-acetamidefuro[3,2-b]pyridine trifluoroacetate;
13) 2-methyl-3-(2-[N'-methyl-N'-([6-carboxamidopyrazin-2-yl]methyl)amino]ethyl)-5-propanecarboxamidefuro[3,2-b]pyridine;
14) 2-methyl-3-(2-[N'-methyl-N'-([5-nitropyrimidin-2-yl]methyl)amino]ethyl)-5-(2-propanecarboxamide)furo[3,2-b]pyridine;
15) 2-methyl-3-(2-[N'-methyl-N'-([5-dimethylaminopyridazin-3-yl]methyl)amino]ethyl)-5-butyramidefuro[3,2-b]pyridine benzoate;
16) 2-methyl-3-(2-[N'-methyl-N'-([indazol-5-yl]methyl)amino]ethyl)-5-pentanecarboxamidefuro[3,2-b]pyridine;
17) 2-methyl-3-(2-[N'-methyl-N'-([quinolin-4-yl]methyl)amino]ethyl)-5-cyclopropanecarboxamidefuro[3,2-b]pyridine;
18) 2-methyl-3-(2-[N'-methyl-N'-([isoquinolin-7-yl]methyl)amino]ethyl)-5-cyclobutanecarboxamidefuro[3,2-b]pyridine;
19) 2-methyl-3-(2-[N'-methyl-N'-([quinoxalin-2-yl]methyl)amino]ethyl)-5-cyclopentanecarboxamidefuro[3,2-b]pyridine hexanoate;
20) 2-methyl-3-(2-[N'-methyl-N'-([quinaxolin-5-yl]methyl)amino]ethyl)-5-cyclohexanecarboxamidefuro[3,2-b]pyridine;
21) 2-methyl-3-(2-[N'-methyl-N'-([thiazol-2-yl]methyl)amino]ethyl)-5-cycloheptanecarboxamidefuro[3,2-b]pyridine;
22) 2-methyl-3-(2-[N'-methyl-N'-([2-aminobenzothiazol-5-yl]methyl)amino]ethyl)-5-(4-fluorobenzamide)furo[3,2-b]pyridine trifluoromethanesulfonate;
23) 2-methyl-3-(2-[N'-methyl-N'-([oxazol-5-yl]methyl)amino]ethyl)-5-(3-iodobenzamide)furo[3,2-b]pyridine;
24) 2-methyl-3-(2-[N'-methyl-N'-([6-nitrobenzoxazol-2-yl]methyl)amino]ethyl)-5-(2-chlorobenzamide)furo[3,2-b]pyridine hydrobromide;
25) 2-methyl-3-(2-[N'-methyl-N'-([1,4-benzodioxan-6-yl]methyl)amino]ethyl)-5-(2-chloropyridine-3-carboxamide)furo[3,2-b]pyridine;
26) 2-isopropyl-3-(2-[N'-methyl-N'-([isoxazol-4-yl]methyl)amino]ethyl)-5-benzamidefuro[3,2-b]pyridine;
27) 2-methyl-3-(2-[N'-methyl-N'-([benzisoxazol-3-yl]methyl)amino]ethyl)-5-(thiophene-2-carboxamide)furo[3,2-b]pyridine;
28) 2-methyl-3-(2-[N'-methyl-N'-([1,3,4-oxadiazol-2-yl]methyl)amino]ethyl)-5-(furyl-3-carboxamide)furo[3,2-b]pyridine;
29) 2-methyl-3-(2-[N'-methyl-N'-([1,2,3-triazol-4-yl]methyl)amino]ethyl)-5-(4-fluorobenzamide)furo[3,2-b]pyridine tosylate;
30) 3-(2-[N'-methyl-N'-((4-bromothien-2-yl)methyl)amino]ethyl)-5-(4-fluorobenzamide)furo[3,2-b]pyridine hydrochloride;
31) 2-ethyl-3-(2-[N'-ethyl-N'-((3-methylthiobenzofur-5-yl)ethyl)amino]ethyl)-5-(pyridine-2-carboxamide)furo[3,2-b]pyridine;
32) 2-propyl-3-(2-[N'-isopropyl-N'-1-((isobenzofur-2-yl)prop-3-yl)amino]ethyl)-5-(4-fluorobenzamide)furo[3,2-b]pyridine;
33) 2-methyl-3-(2-[N'-butyl-N'-(pyrrol-3-yl)methyl)amino]ethyl)-5-(4-fluorobenzamide)furo[3,2-b]pyridine maleate;
34) 2-methyl-3-(2-[N'-methyl-N'-((5-cyanoimidazol-2-yl)methyl)amino]ethyl)-5-(4-acetamide)furo[3,2-b]pyridine trifluoroacetate;
35) 2-methyl-3-(2-[N'-methyl-N'-((6-carboxamidopyrazin-2-yl)methyl)amino]ethyl)-5-propanecarboxamidefuro[3,2-b]pyridine;

36) 2-methyl-3-(2-[N'-methyl-N'-((5-nitropyrimidin-2-yl)methyl)amino]ethyl)-5-(2-propanecarboxamide)furo[3,2-b]pyridine;
37) 2-methyl-3-(2-[N'-methyl-N'-((5-dimethylaminopyridazin-3-yl)methyl)amino]ethyl)-5-butanecarboxamidefuro[3,2-b]pyridine benzoate;
38) 2-methyl-3-(2-[N'-methyl-N'-((indazol-5-yl)methyl)amino]ethyl)-5-pentanecarboxamidefuro[3,2-b]pyridine;
39) 2-methyl-3-(2-[N'-methyl-N'-((2-aminobenzothiazol-5-yl)methyl)amino]ethyl)-5-(4-fluorobenzamide)furo[3,2-b]pyridine trifluoromethanesulfonate;
40) 2-methyl-3-(2-[N'-methyl-N'-(2-[pyridin-4-yl]ethyl)amino]ethyl)-5-(N-ethylurea)furo[3,2-b]pyridine;
41) 2-methyl-3-(2-[N'-methyl-N'-s-butylamino]ethyl)-5-(N-isopropylurea)furo[3,2-b]pyridine;
42) 2-methyl-3-(2-[N'-methyl-N'-(2-[pyridin-4-yl]ethyl)amino]ethyl)-5-[N-[(3-methoxy)phenyl]urea]furo[3,2-b]pyridine malonate.

While all enantiomers, diastereomers, and mixtures thereof, are useful as $5\text{-}HT_{1F}$ agonists, single enantiomers and single diastereomers are preferred. Furthermore, while all of the compounds of this invention are usefulias $5\text{-}HT_{1F}$ agonists, certain classes are preferred. The following paragraphs describe such preferred classes.

1) R is moiety (a);
2) R is moiety (b);
3) R is moiety (c);
4) E—D is CH—$CH_2$;
5) E—D is C=CH;
6) $R^1$ is hydrogen;
7) $R^1$ is $C_1$–$C_4$ alkyl;
8) $R^1$ is methyl;
9) $R^2$ is hydrogen;
10) $R^2$ is halo;
11) $R^2$ is hydroxy;
12) $R^2$ is —$NR^3R^4$;
13) $R^2$ is —$SR^3$;
14) $R^2$ is —$C(O)R^3$;
15) $R^2$ is —$C(O)NR^3R^4$;
16) $R^2$ is —$NR^3SO_2R^5$;
17) $R^2$ is —$NHC(Q)NR^3R^4$;
18) $R^2$ is —$NHC(Q)NR^3R^4$, and Q is S;
19) $R^2$ is —$NHC(Q)NR^3R^4$, and Q is O;
20) $R^2$ is —$NHC(O)OR^3$;
21) $R^2$ is —$NR^3C(O)R^5$;
22) $R^2$ is —$NR^3R^4$ and $R^3$ and $R^4$ are taken together with the nitrogen to which they are attached are selected from the group consisting of pyrrolidine, piperidine, piperazine, morpholine, or thiomorpholine;
23) $R^3$ is hydrogen;
24) $R^3$ is $C_1$–$C_4$ alkyl;
25) $R^3$ is methyl;
26) $R^3$ is $C_2$–$C_6$ alkenyl;
27) $R^3$ is $C_2$–$C_6$ alkynyl;
28) $R^3$ is —$(CH_2)_n$aryl;
29) $R^4$ is hydrogen;
30) $R^4$ is $C_1$–$C_4$ alkyl;
31) $R^4$ is $C_2$–$C_6$ alkenyl;
32) $R^4$ is $C_2$–$C_6$ alkynyl;
33) $R^4$ is —$(CH_2)_n$aryl;
34) $R^5$ is hydrogen;
35) when R is $CH_2CH_2NR^3R^4$, $R^3$ is hydrogen and $R^4$ is methyl;
36) when R is $CH_2CH_2NR^3R^4$, $R^3$ is methyl and $R^4$ is methyl; $R^2$ is selected from the group consisting of benzoylamino, propanoylamino, 4-fluorobenzoylamino, 2-thienoylamino, and 2,4-difluorobenzoylamino;
37) $R^3$ is methyl;
38) $R^3$ is ethyl;
39) $R^3$ is propyl;
40) $R^3$ is isopropyl;
41) $R^3$ is phenyl;
42) $R^3$ is allyl;
43) $R^3$ is phenyl monosubstituted with halo;
44) $R^3$ is 4-fluorophenyl;
45) $R^3$ is 4-chlorophenyl;
46) $R^3$ is phenyl ($C_1$–$C_4$ alkylene)
47) $R^3$ is benzyl;
48) $R^3$ is phenethyl;
49) $R^3$ and $R^4$ taken together with the nitrogen to which they are attached form a morpholine ring;
50) $R^3$ and $R^4$ taken together with the nitrogen to which they are attached form a thiomorpholine ring;
51) $R^3$ and $R^4$ taken together with the nitrogen to which they are attached form a pyrrolidine ring;
52) $R^3$ and $R^4$ taken together with the nitrogen to which they are attached form a piperidine ring;
53) $R^3$ and $R^4$ taken together with the nitrogen to which they are attached form a piperazine ring;
54) $R^3$ and $R^4$ taken together with the nitrogen to which they are attached form a 4-substituted piperazine ring;
55) $R^3$ is methyl;
56) $R^3$ is ethyl;
57) $R^3$ is propyl;
58) $R^3$ is allyl;
59) $R^3$ is phenyl monosubstituted with $C_1$–$C_4$ alkoxy;
60) $R^3$ is 4-methoxyphenyl;
61) $R^3$ is phenyl;
62) any compound exemplified;
63) the compound is an acid addition salt;
64) the compound is the hydrochloride salt;
65) the compound is the oxalate salt; and
66) the compound is the fumarate salt.

It will be understood that the above classes may be combined to form additional preferred classes.

It is preferred that the mammal to be treated by the administration of compounds of this invention is human.

The synthetic methodology required to prepare the compounds of the invention is well known to those skilled in the art. A suitable electrophile is reacted with an appropriate 5-aminofuro[3,2-b]pyridine to provide the corresponding ureas, thioureas, sulfonamides, carbamates, and carboxamides of the present invention. This chemistry is illustrated in Scheme 1 where R, $R^1$, $R^3$, $R^4$, and $R^5$ are as described supra.

Scheme 1

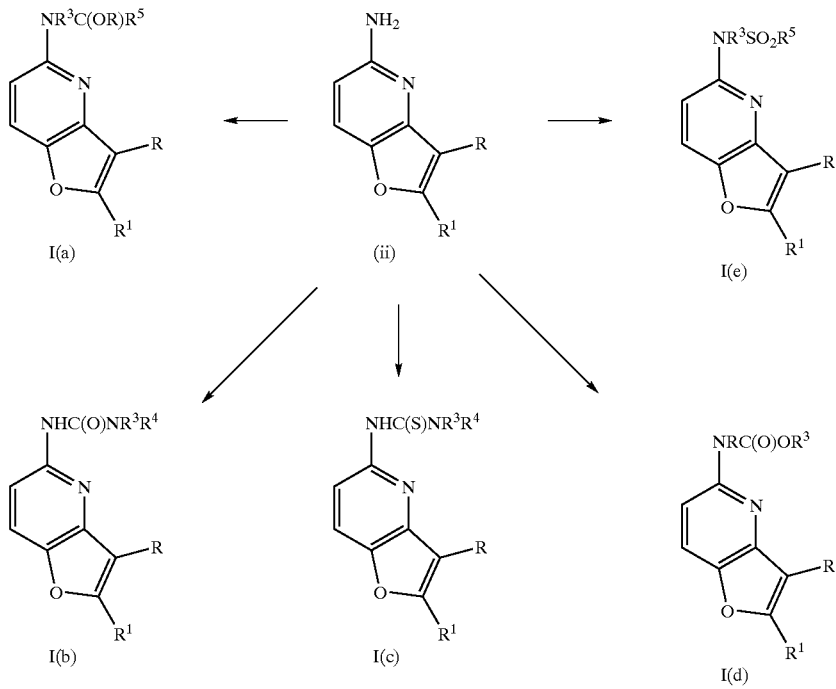

To prepare compounds of the invention where $R^2$ is —$NR^3SO_2R^5$, formula I(e), a solution of the appropriate 5-aminofuro[3,2-b]pyridine in suitable solvent, such as tetrahydrofuran, dioxane, diethyl ether or dimethylformamide, at a temperature from about 0° C. to about ambient, is reacted with a commercially available $R^5$-sulfonyl halide or $R^5$-sulfonic anhydride in the presence of a suitable base such as pyridine or triethylamine. The resultant sulfonamide may be isolated by dilution of the reaction mixture with water, adjustment of pH, and extraction with a water immiscible solvent such as dichloromethane. The product may be used for further reactions as recovered, or may be purified by chromatography, or by recrystallization from a suitable solvent.

Compounds of the invention where $R^2$ is —NHC(Q) $NR^3R^4$, I(b)/I(c), are prepared by treating a solution of the appropriate 5-aminofuro[3,2-b]pyridine (ii) in a suitable solvent, such as chloroform or dichloromethane, with an appropriate isocyanate, isothiocyanate, carbamoyl chloride or carbamoyl bromide. Appropriate carbamoyl chlorides are available by treating an amine of formula $NHR^3R^4$ with phosgene. When a carbamoyl chloride or carbamoyl bromide is used, the reactions are performed in the presence of a suitable base. Suitable bases include amines typically used as acid scavengers, such as pyridine or triethylamine, or commercially available polymer bound bases such as polyvinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds of the invention which are ureas may be converted into the corresponding thiourea by treatment with [2,4-bis(4-methoxyphenyl)-1,3-dithia-2,4-diphosphetane-2,4-disulfide](Lawesson's Reagent) or phosphorus pentasulfide.

Compounds of the invention where $R^2$ is $R^3C(O)NH$— I(a) or —$NR^3C(O)OR^5$ I(d) are prepared by treating the desired 5-aminofuro[3,2-b]pyridine (ii) with either an appropriate carboxylic acid chloride, bromide or anhydride, or an appropriately substituted chloroformate optionally in the presence of an acylation catalyst such as dimethylaminopyridine, in the presence of a suitable base. Suitable bases include amines typically used as acid scavengers, such as pyridine or triethylamine, or commercially available polymer bound bases such as polyvinylpyridine. When an excess of the electrophile is necessary to ensure complete reaction of the amine, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture to remove the polymer bound constituents, and then concentration of the filtrate under reduced pressure to isolate the desired product. The product from these reactions may be purified chromatographically or recrystallized from a suitable solvent if desired.

Alternatively, compounds of the invention where $R^2$ is —$NR^3C(O)R^5$ I(a) or —$NHC(O)OR^3$ I(d) may be prepared by reacting the 5-aminofuro[3,2-b]pyridine (ii) with an appropriate carboxylic acid in the presence of a typical peptide coupling reagent such as N,N'-carbonyldiimidazole (CDI), N,N'-dicyclohexyl-carbodiimide (DCC) and 1-(3-dimethylaminopropyl)-3-ethylcarbodiimide hydrochloride (EDC). Polymer supported forms of carbodiimide peptide coupling reagents are useful for the preparation of compounds of the present invention. A polymer supported form of EDC, for example, has been described (*Tetrahedron Letters*, 34 (48), 7685 (1993)). Additionally, a new carbodiimide coupling reagent, 1-(3-(1-pyrrolidinyl)propyl)-3-ethylcarbodiimide (PEPC), and its corresponding polymer supported forms have been discovered and are very useful for the preparation of the compounds of the present invention.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethyl-phenylacetamidomethyl resin (Pam Resin) and 4-benzyloxybenzyl alcohol resin (Wang Resin) available from Advanced Chemtech of Louisville, Ky. (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis. (see Aldrich 1994–1995 catalog, page 899).

Methods for the preparation of PEPC and its polymer supported forms are outlined in the following scheme.

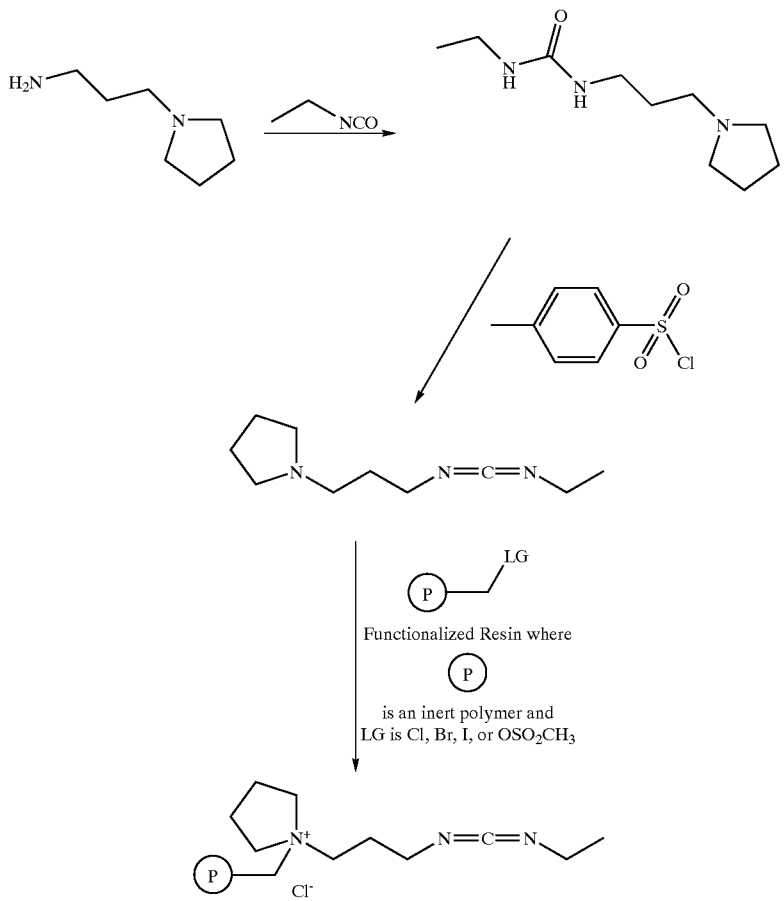

Briefly, PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient to about 45° C., for from about three hours to about three days. Typically, the product may be isolated by washing the reaction with water and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

The 5-aminofuro[3,2-b]pyridines (ii) required for the preparation of the compounds of the present invention may be prepared by methods well known to one of ordinary skill in the art. Compounds of the invention where R is moiety (a) are derived from the corresponding 5-aminofuro[3,2-b] pyridines which may be prepared by the procedure described in Scheme 2 where $R^1$, $R^3$ and $R^4$ are as previously defined.

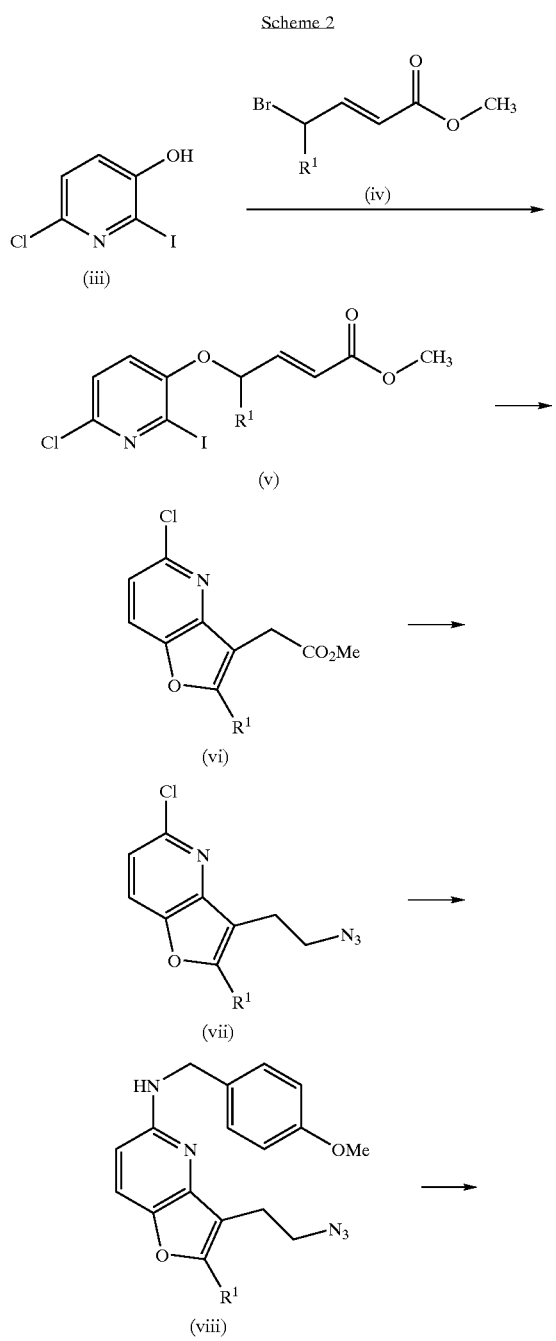

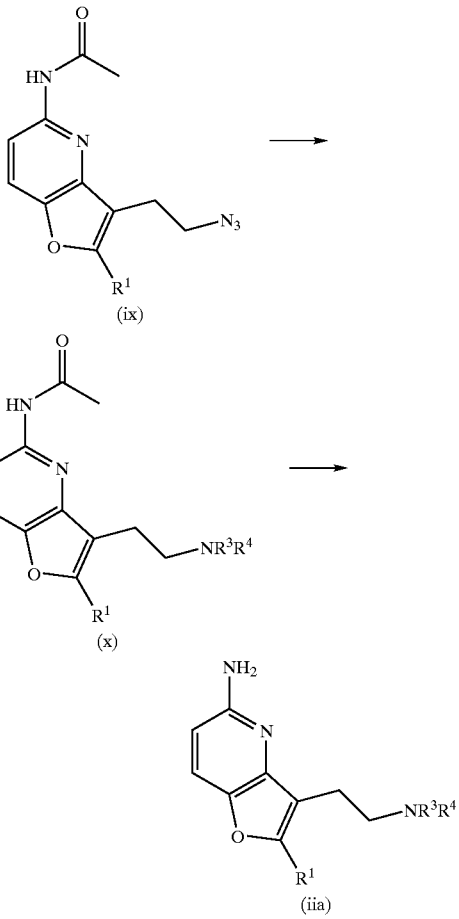

6-Chloro-2-iodo-3-hydroxypyridine (iii) and an appropriate ester, such as methyl 4-bromocrotonate (iv) or ethyl 4-bromo-2-pentenoate, are combined in an appropriate solvent, typically tetrahydrofuran, dimethylformamide or N-methylpyrrolidinone with a suitable base, typically potassium or sodium carbonate, pyridine or triethylamine, and the reaction mixture heated to reflux until all of the starting substituted pyridine has reacted. The resulting compound of formula (v) may then be used directly or purified by crystallization or chromatography. As the skilled artisan would appreciate, the compound of formula (vi) may be prepared through a coupling reaction of a compound of formula (v), see Larock, et al., *Tetrahedron Letters*, 1988, 29:4687–4690.

Compounds of the invention where R is —CH$_2$CH(R$^5$)NR$^3$R$^4$ are prepared from compounds of formula (vi). One method of such preparation may first consist of converting the ester to an alcohol and then converting the alcohol to an azidoalkane. Such methods may be found in Larock, *Comprehensive Organic Transformations*, 1989, pp 419. The resulting compound of formula (vii) may then be used directly or purified by crystallization or chromatography. The resulting compound of formula (vii) may then be aminated at the halo group, see Buchwald, et al., *Journal of the American Chemical Society*, 1997, 119:10539–10540. The resulting compound of formula (viii) may then be used directly or purified by crystallization or chromatography. The amine of formula (viii) may then be converted to amide of formula (ix) by procedures well known to the skilled artisan, see Larock, *Comprehensive Organic Transformations*, 1989, pp 859. The resulting compound of formula (ix) may then be used directly or purified by crystallization or chromatography. The azide of formula (ix) may then be reduced by catalytic hydrogenation over palladium with an appropriate aldehyde and, if desired, purified by crystallization or chromatography. While the acetamide moiety (x) may be hydrolyzed during the hydrogenation step, the desired 5-aminofuro[3,2-b]pyridine (iia) may be prepared in a separate hydrolysis step if necessary.

The 6-chloro-3-hydroxy-2-iodopyridine compounds of formula iii may be prepared from commercially available 2-chloro-4-aminopyridine by well known methodology. The amine substituent of 2-chloro-4-aminopyridine may be first converted to the acetate ester via diazonium salt formation followed by quenching with acetic anhydride. The ester group may then be hydrolyzed under standard conditions; see for example, Greene, "Protective Groups in Organic Synthesis, pg. 162; to liberate the hydroxy group.

The compounds of formula xii may be prepared from compounds of formula xvi as illustrated in Scheme 4 below where $R^7$ is amino, nitro, chloro, bromo, or hydroxy, and $R^1$, and $R^3$ are as defined above.

Scheme 3

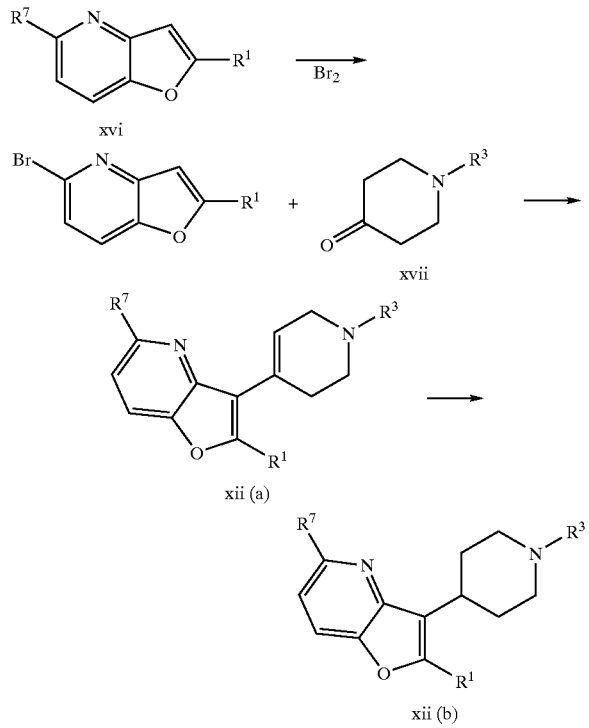

For furo[3,2-b]pyridine compounds of formula xii(a) the reaction may be performed by first reacting a furo[3,2-b] pyridine of formula xvi where $R^7$ is amino or preferably nitro with bromine in acetic acid. The reaction is typically performed at about 50° C. for about 4 hours. After the bromination is substantially complete, the volatiles are then removed under reduced pressure and the residue is subjected to an extractive work-up under basic conditions. The resulting 3-bromofuro[3,2-b]pyridine in diethyl ether is then treated with an alkyl lithium, typically-n-butyl lithium, in the same solvent, below −100° C. to affect a metal-halogen exchange. After stirring at this temperature for about 1 hour, the reaction mixture is treated with an equivalent of an appropriate compound of formula xvii. Once the addition of the compound of formula xvii is complete, the reaction mixture is stirred below −78° C. for an additional 3 to 5 hours. It is critical, when $R^1$ is hydrogen, to maintain the reaction mixture at this temperature to avoid equilibration of the anion to the 2-position of the benzofuran ring. The reaction mixture is then allowed to warm to −20° C. over about 50 minutes. An excess of an appropriate base, preferably sodium or potassium hydroxide, in a lower alkanol, typically methanol or ethanol is then added and the reaction refluxed for 0.25 to 24 hours to provide a benzofuran compound of formula xii(a) where $R^7$ is amino or nitro.

If desired, compounds of formula xii(a) may be hydrogenated over a precious metal catalyst to give the corresponding compounds of formula xii(b). When $R^7$ is bromo, a catalyst such as sulfided platinum on carbon, platinum oxide, or a mixed catalyst system of sulfided platinum on carbon with platinum oxide may be used to prevent hydrogenolysis of that bromo substituent during the reduction. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20 p.s.i. to 80 p.s.i., preferably from 50 p.s.i. to 60 p.s.i., at 0° C. to 60° C., preferably at ambient temperature to 40° C., for 1 hour to 3 days. Additional charges of hydrogen may be required to drive the reaction to completion depending on the specific substrate.

When the hydrogenation is performed with a compound of formula xii(a) where $R^7$ is amino or nitro, more vigorous hydrogenation conditions may be used without disrupting the rest of the molecule. For example, a catalyst such as platinum or palladium on carbon may be utilized without substantially effecting deleterious side reactions.

In general, when $R^7$ is nitro, that nitro group may be reduced to an amine at any convenient point in the syntheses outlined in Scheme 3 by well known methodology. See, e.g., Larock, "Comprehensive Organic Transformations", pgs. 412–415, VCH Publishers, New York, N.Y., 1989. Additionally, when $R^7$ is nitro in compounds of formula xii(a), that nitro group and the double bond may be hydrogenated simultaneously if desired to give a compound of formula xii(b) where $R^7$ is amino by many of the methods described by Larock for the nitro group alone. Furthermore, methods for selective reduction of a double bond in the presence of a nitro group are known in the art.

When $R^7$ is amino, that amino group may be converted to an oxo group via methods well known to the skilled artisan at any convenient point in the syntheses outlined in Scheme 3. The amino group may first be treated with sodium nitrate and $H^+$ and then with $POBr_3$ to covert the amino group to bromo. If needed, it is preferred to perform the reaction after the conversion of a compound of formula xii(a) to a compound of formula xii(b).

When $R^7$ is hydroxy, that free hydroxy group may have a trifluoromethanesulfonyl group ($SO_2CF_3$) installed by standard procedures known in the art at any convenient point in the syntheses outlined in Scheme 3. For example, a compound of formula xii(a) where $R^7$ is hydroxy may be reacted with trifluoromethanesulfonyl chloride or trifluoromethanesulfonic anhydride in the presence of an appropriate base to give a compound of formula xii(a) where $R^7$ is $OSO_2CF_3$.

Compounds of formula xvi may be prepared by known procedures such as that described in Scheme 4 below where $R^1$ and $R^7$ are as defined above.

Scheme 4

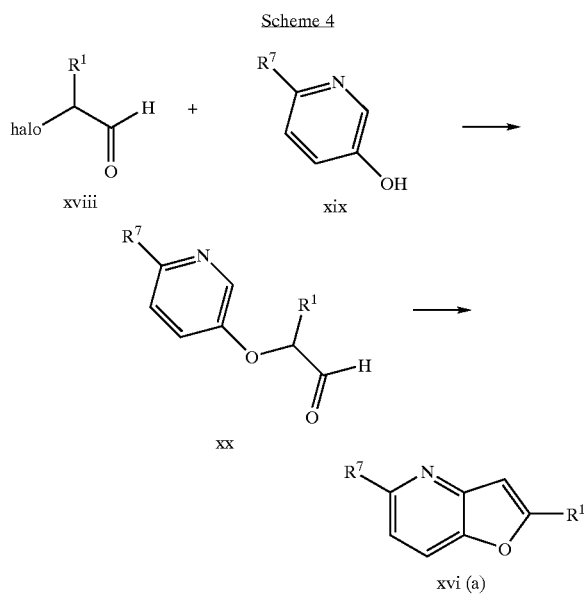

An a-halo-acetaldehyde of formula xviii, optionally protected as the corresponding acetal, may be reacted with an appropriately substituted, commercially available, hydroxy-pyridine of formula xix under standard alkylating conditions to provide the corresponding ether of formula X. This ether may be converted to a benzofuran of formula xvi(a) by heating a compound of formula xx in the presence of an acid, typically polyphosphoric acid or sulfuric acid. When $R^7$ is amino in compounds of formula xix or xx, that amino group should be protected with an appropriate amino protecting group as described in Greene. The protecting group may be chosen such that it is hydrolyzed during the cyclization step or, if desired, the unprotected compounds of formula xvi(a) where $R^7$ is amino may be prepared in a separate deprotection step if necessary. Furthermore, these amino compounds of formula xvi(a) may be converted to the corresponding halo compounds via the Sandmeyer reaction.

Compounds of formula xvii where R is an indolizine may be prepared from methylvinyl ketone and an appropriate amino-dialkylacetal or -cyclic acetal according to the procedures found in *Tet. Let.*, 24:3281, 1983, and *J. C. S. Perk. I*, 447, 1986. These acetals are generally commercially available or can be synthesized by well known methods in the art from their corresponding commercially available 4-substituted butanals. This chemistry is illustrated in Scheme 5, $R^8$ and $R^9$ are $C_1$–$C_4$ alkyl or $R^8$ and $R^9$ taken together with the oxygen atoms, to which they are attached, form a 5 or 6 membered cyclic acetal.

Scheme 5

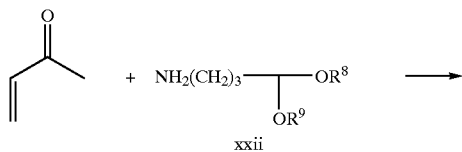

Compounds of formula xvii(a) may be prepared by acid treatment of the addition product of methyl vinyl ketone and a compound of formula xxi. A diethylacetal of formula xxi is a preferred starting material for this reaction ($R^9$ and $R^8$ are ethyl). The reaction may be performed by first dissolving an appropriate aminoacetal of formula xxiii in an suitable solvent, typically diethyl ether at 0° C., and then adding approximately 1.7 equivalents of methyl vinyl ketone. Typically the reaction is allowed to stir at 0° C. for approximately 2 hours before acidification by addition of, or extraction with, aqueous hydrochloric acid. Usually, the organic layer is removed before heating the aqueous layer to approximately 100° C. for 1 hour. The resulting compounds of formula xvii(a) may be isolated from the reaction mixture by adjusting the pH of the solution to alkaline and extracting with a water immiscible solvent such as ethyl acetate or dichloromethane.

Compounds of formula xvii(a) prepared as described in Scheme 5 are racemic and, if used as described in Scheme 3 will produce racemic compounds of the invention. Compounds of the invention that are optically enhanced in one enantiomer may be obtained by resolving the compounds of. formula xvii(a) before use of these compounds as described in Scheme 5. Methods of resolving enantiomeric compounds of this type are well known in the art. For example, resolution can be achieved by use of chiral chromatography. Furthermore, racemic compounds of formula xvii(a) may be converted to their corresponding diastereomeric mixture of salts by reaction with a chiral acid such as (+) or (−) tartaric acid. The diastereomers may then be separated and purified by recrystallization. Once separated, the salts may each be converted back to the chiral free base compounds of formula xvii(a) by reacting the salts with an aqueous base, such as sodium hydroxide, then extracting the mixture with a common organic solvent. The optical purity in resolved compounds of formula xvii(a) is maintained while undergoing the chemistry described in this application to afford optically pure compounds of the invention. As an alternative, when advantageous, the resolution techniques just discussed may be performed at any convenient point in the syntheses described in Schemes 4–5.

The α-halo aldehydes, or corresponding acetals of formula xviii are either commercially available or may be prepared from the corresponding acids or acid halides by methods well known to one of ordinary skill in the art. This chemistry is reviewed by Larock, "Comprehensive Organic Transformations," pages 378–379, VCH Publishers, New York, 1989. Compounds of formula xiii, xvi, xvii, xviii, xix, and xxi are known in the art and, to the extent not commercially available, are readily synthesized by standard procedures commonly employed in the art such as those described herein.

The optimal time for performing the reactions of Schemes 1–6 may be determined by monitoring the progress of the reaction via conventional chromatographic techniques, e.g., thin layer chromatography and high performance liquid chromatography. Furthermore, it is usually preferred to conduct the reactions of Scheme 1–6 under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The intermediate compounds of this invention are preferably purified before their use in subsequent reactions. The intermediates and final products may be purified when, if in the course of their formation, they crystallize out of the reaction solution. In such a situation, the precipitate may be collected by filtration and washed with an appropriate solvent. Certain impurities may be removed from the organic reaction mixture by aqueous acidic or basic extraction followed by removal of the solvent by extraction, evaporation, or decantation. The intermediates and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same.

Preparation 1

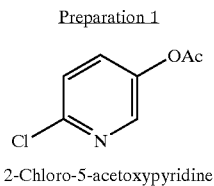

2-Chloro-5-acetoxypyridine

To a solution of 2-chloro-5-aminopyridine (30.0 g, 230 mmol) cooled to −10° C. in 120 mL of 3:1 1,2-dimethoxyethane/dichloromethane was added 62.1 mL of boron trifluoride diethyl etherate (490 mL) followed by a solution of isobutyl nitrite (32.3 mL, 276 mmol) dissolved in 30 mL of 1,2-dimethoxyethane. The reaction was maintained at −10° C. for 0.25 h then allowed to warm to room temperature over 0.5 h. The mixture was diluted with pentane, cooled to 0° C. and filtered. The ivory, solid was washed with cold pentane, dried in vacuo, and used immediately without further purification.

The tetrafluoroborate diazonium salt was dissolved in 300 mL of acetic anhydride and heated at 75° C. for 2.5 h. The reaction was cooled, concentrated in vacuo, and partitioned between diethyl ether and saturated aqueous NaHCO$_3$. The aqueous layer was extracted with diethyl ether, and the combined organics were washed with saturated aqueous NaCl, dried (MgSO$_4$), and concentrated in vacuo. The resulting brown residue was chromatographed (10% ethyl acetate/hexane) to provide 24.6 g (62%) of the desired material as a white solid.

Calculated for C$_7$H$_6$ClNO$_2$: Theory: C, 49.00; H, 3.52; N, 8.16; Found: C, 49.29; H, 3.47; N, 8.12.

Preparation 2

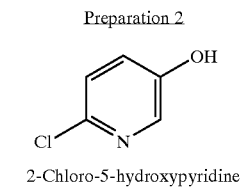

2-Chloro-5-hydroxypyridine

2–Chloro-5-acetoxypyridine (21.66 g, 126 mmol) was dissolved in 300 mL of methanol and K$_2$CO$_3$ (8.70 g, 63 mmol) was added. The reaction was stirred at room temperature for approx. 2 h, then concentrated in vacuo. The residue was diluted with diethyl ether and water, and the aqueous layer was adjusted to neutral pH by the addition of 1N aqueous HCl. Following extraction with diethyl ether, the organics were combined, washed with a solution of saturated aqueous NaCl, dried with MgSO$_4$, and concentrated in vacuo. The resulting yellow solid (15.58 g, 96%) was used without further purification.

Preparation 3

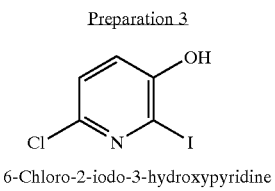

6-Chloro-2-iodo-3-hydroxypyridine

A solution of the above material (15.48 g, 119 mmol) and Na$_2$CO$_3$ (26.56 g, 251 mmol) in water (300 mL) was charged with iodine (30.3 g, 119 mmol). The reaction mixture was stirred at room temperature until the iodine color disappeared, approx. 48 h. The solution was adjusted to pH =5 with 1 N aqueous HCl, and extracted with ethyl acetate. The organic layers were washed with saturated aqueous NaCl, dried over Na$_2$SO$_4$, and concentrated in vacuo.

The resulting white solid was recrystallized from methanol to provide 17.8 g (95%) of the title compound.

MS(m/e): 256 (M$^+$); Calculated for C$_5$H$_3$ClINO: Theory: C, 23.51; H, 1.18; N, 5.48; Found: C, 23.72; H, 1.19; N, 5.45.

Preparation 4

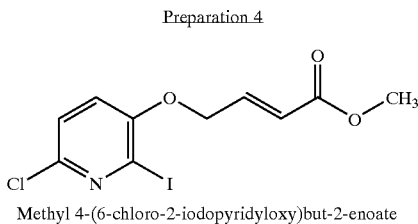

Methyl 4-(6-chloro-2-iodopyridyloxy)but-2-enoate

A mixture of 6-Chloro-2-iodo-3-hydroxypyridine (10.0 g, 39 mmol), methyl 4-bromocrotonate (14 mL, 117 mmol), and K$_2$CO$_3$ (16.2 g, 117 mmol) in 250 mL of N,N-dimethylformamide was heated at 60° C. for 4 h. The reaction was cooled, concentrated in vacuo and partitioned between chloroform and water. Following extraction with chloroform and washing with saturated aqueous NaCl, the organics were dried over Na$_2$SO$_4$ and concentrated in vacuo. Column chromatography (0%→30% ethyl acetate/hexane) provided the desired compound (13.3 g, 97%) as a white solid.

m.p.=112–114° C.; Calculated for C$_{10}$H$_9$ClINO$_3$: Theory: C, 33.97; H, 2.57; N, 3.96; Found: C, 34.27; H, 2.72; N, 3.95.

Preparation 5

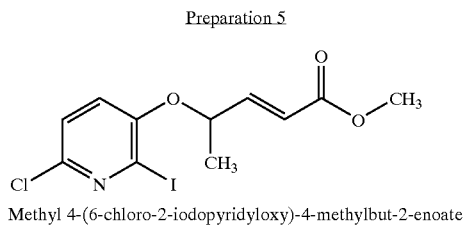

Methyl 4-(6-chloro-2-iodopyridyloxy)-4-methylbut-2-enoate

The title compound was prepared in 99% isolated yield in the same manner as methyl 4-(6-chloro-2-iodopyridyloxy) but-2-enoate, utilizing methyl 4-bromo-2-pentenoate (Löffler, A. et al. Helv. Chim. Acta, 1970, 53, 403–417) as the electrophile.

MS(m/e): 368 (M+); Calculated for $C_{11}H_{11}ClINO_3$: Theory: C, 35.94; H, 3.02; N, 3.81; Found: C, 35.70; H, 2.97; N, 3.81.

Preparation 6

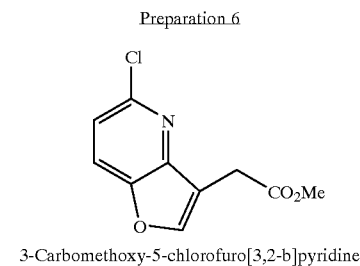

3-Carbomethoxy-5-chlorofuro[3,2-b]pyridine

To a solution of methyl 4-(6-chloro-2-iodopyridyloxy) but-2-enoate (5.87 g, 16.6 mmol) dissolved in 150 mL of N,N-dimethylformamide was added 4.39 g of $Na_2CO_3$ (42 mmol), 1.13 g of sodium formate (16.6 mmol), 5.07 g of tetrabutylammonium chloride (18.0 mmol), and 0.19 g of palladium(II) acetate (0.8 mmol). The reaction mixture was heated at 80° C. for 3 h, then concentrated in vacuo. The residue was partitioned between chloroform and water, and the aqueous layer was extracted with chloroform. The combined organics were washed with saturated aqueous NaCl, dried over $Na_2SO_4$, and concentrated. Upon column chromatography (0%→40% ethyl acetate/hexane), the desired compound was isolated as an ivory solid (3.66 g, 98%).

m.p.=92–93° C.; MS(m/e): 226 (M+); Calculated for $C_{10}H_8ClNO_3$: Theory: C, 53.23; H, 3.57; N, 6.21; Found: C, 53.20; H, 3.61; N, 5.96.

Preparation 7

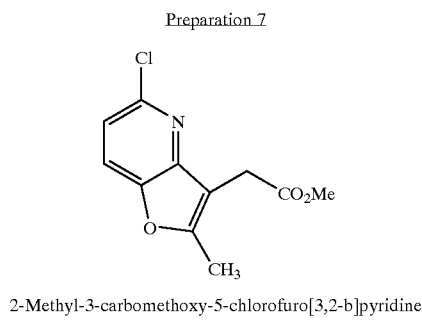

2-Methyl-3-carbomethoxy-5-chlorofuro[3,2-b]pyridine

The title compound was prepared in 70% isolated yield in the manner described in Preparation 6.

m.p.=166–167° C.; MS(m/e): 240 (M+); Calculated for $C_{11}H_{10}ClNO_3$: Theory: C, 55.13; H, 4.21; N, 5.84; Found: C, 55.18; H, 4.07; N, 6.07.

Preparation 8

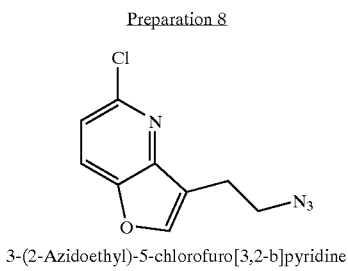

3-(2-Azidoethyl)-5-chlorofuro[3,2-b]pyridine

To a solution of 3-carbomethoxy-5-chlorofuro[3,2-b] pyridine (3.0 g, 13 mmol) cooled to −78° C. in tetrahydrofuran (125 mL) was added diisobutylaluminum hydride (1 M in hexane, 40 mL, 40 mmol). The reaction mixture was maintained at −78° C. for 0.25 h, warmed to room temperature over a period of 1 h, then poured into a solution of 2 M aqueous sodium potassium tartrate. After stirring vigorously at room temperature overnight, the aqueous layer was extracted with ethyl acetate. The combined organics were washed with saturated aqueous NaCl, dried over $Na_2SO_4$, and concentrated in vacuo.

The resulting crude alcohol was cooled to 0° C. in dichloromethane (150 mL), and charged with triethylamine (4.1 mL, 29 mmol) followed by methanesulfonyl chloride (1.4 mL, 17 mmol). The reaction was warmed to room temperature and stirred for 2 h, then poured into a saturated solution of $NaHCO_3$. Following extraction with dichloromethane, the organic layer was washed with saturated aqueous NaCl, dried over $Na_2SO_4$, and concentrated to provide an amber oil.

To the crude mesylate dissolved in N,N-dimethylformamide (100 mL) was added sodium azide (2.6 g, 40 mmol). The reaction was stirred at room temperature overnight, then poured into water. The mixture was extracted with ethyl acetate, and the combined organics were washed with saturated aqueous NaCl, dried over $Na_2SO_4$, and concentrated. Column chromatography (0→20% ethylacetate/hexane) provided the desired azide (2.4 g, 80%).

m.p.=55–57° C.; Calculated for $C_9H_7ClN_4O$: Theory: C, 48.55; H, 3.17; N, 25.17; Found: C, 48.74; H, 3.13; N, 25.43.

Preparation 9

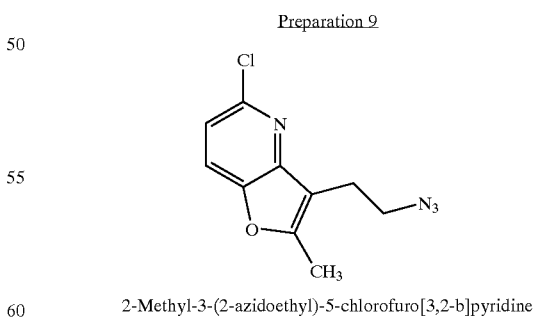

2-Methyl-3-(2-azidoethyl)-5-chlorofuro[3,2-b]pyridine

The title compound was prepared in 75% isolated yield in the 3-step procedure described in Preparation 8.

MS(m/e): 237 (M+); Calculated for $C_{10}H_9ClN_4O$: Theory: C, 50.75; H, 3.83; N, 23.67; Found: C, 50.75; H, 3.79; N, 23.65.

Preparation 10

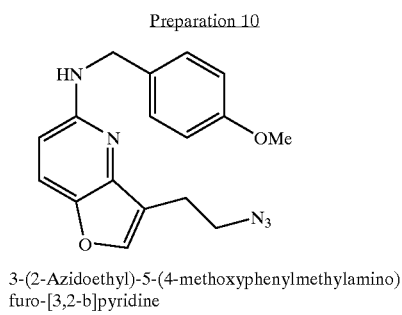

3-(2-Azidoethyl)-5-(4-methoxyphenylmethylamino)furo-[3,2-b]pyridine

A solution of 3-(2-azidoethyl)-5-chlorofuro-[3,2-b]pyridine (2.32 g, 10.40 mmol) dissolved in toluene (300 mL) was treated with tris(dibenzylideneacetone)dipalladium(0) (0.48 g, 0.52 mmol), (±)-2,2′-bis(diphenylphosphino)-1,1′-binaphthyl (BINAP) (0.65 g, 1.04 mmol), sodium tert-butoxide (1.40 g, 14.00 mmol), and 4-methoxybenzylamine (1.73 g, 12.00 mmol). The reaction was heated at 80° C. overnight. Upon cooling to room temperature, the reaction was partitioned between ethyl acetate and water. The aqueous layer was extracted with ethyl acetate, and the combined organics were washed with saturated aqueous NaCl, dried over $Na_2SO_4$, and concentrated. Column chromatography (0→25% ethyl acetate/hexane) provided the title compound as a yellow oil (3.14 g, 93%).

Calculated for $C_{17}H_{17}N_5O_2$: Theory: C, 63.15; H, 5.30; N, 21.66; Found: C, 63.55; H, 5.60; N, 21.33.

Preparation 11

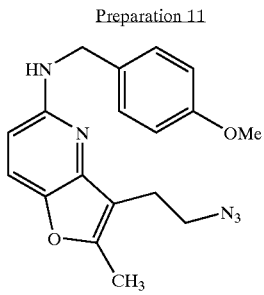

2-Methyl-3-(2-azidoethyl)-5-(4-methoxyphenylmethylamino)furo[3,2-b]pyridine

The title compound was prepared in 79% isolated yield from 2-methyl-3-(2-azidoethyl)-5-chlorofuro[3,2-b]pyridine in the manner described in Preparation 10.

MS(m/e): 338 (M⁺); Calculated for $C_{18}H_{19}N_5O_2$: Theory: C, 64.08; H, 5.68; N, 20.76; Found: C, 64.10; H, 5.94; N, 20.75.

Preparation 12

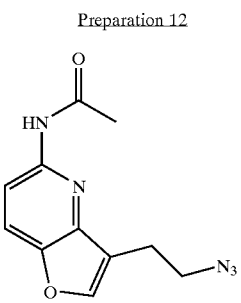

5-Acetylamino-3-(2-azidoethyl)furo[3,2-b]pyridine

To a rapidly stirring mixture of 3-(2-azidoethyl)-5-(4-methoxyphenylmethylamino)furo[3,2-b]pyridine (2.89 g, 8.9 mmol) dissolved in 300 mL of dichloromethane was added water (10 mL) followed by 2,3-dichloro-5,6-dicyano-1,4-benzoquinone (DDQ) (4.68 g, 20.5 mmol). After 2 h at room temperature, a solution of 1 M aqueous $Na_2S_2O_3$ (100 mL) was added, and the reaction was stirred an additional 0.25 h. Following extraction with chloroform, the combined organics were washed with saturated aqueous NaCl, dried over $Na_2SO_4$, and concentrated. The crude amine was purified via solid phase extraction (Varian Mega Bond Elut® SCX column, eluting with 2 M ammonia-methanol), and concentrated in vacuo. The amine was dissolved in pyridine (250 mL) and treated with acetyl chloride (1.05 mL, 13.4 mmol). The reaction was heated at 55° C. for 3 h, then concentrated in vacuo. After partitioning between dichloromethane and 0.1 M aqueous NaOH, the aqueous layer was extracted with dichloromethane, and the combined organic layers were washed with saturated aqueous NaCl, dried over $Mg_2SO_4$, and concentrated in vacuo. Column chromatography on silica gel (0→80% ethyl acetate/hexane) provided the title compound (1.78 g, 81% yield) as a yellow solid.

m.p.=100–101° C.; MS(m/e): 246 (M⁺); Calculated for $C_{11}H_{11}N_5O_2$: Theory: C, 53.87; H, 4.52; N, 28.56; Found: C, 53.96; H, 4.67; N, 28.33.

Preparation 13

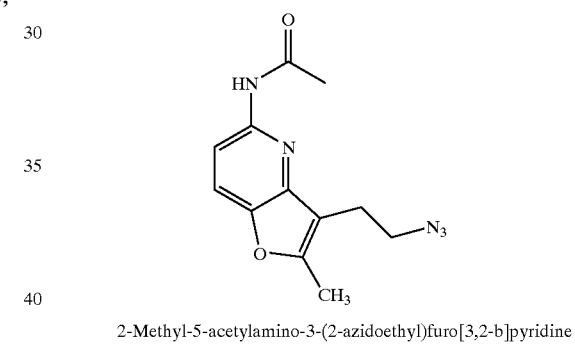

2-Methyl-5-acetylamino-3-(2-azidoethyl)furo[3,2-b]pyridine

The title compound was prepared in 68% isolated yield from 2-methyl-3-(2-azidoethyl)-5-(4-methoxyphenylmethylamino)furo[3,2-b]pyridine using the method described in Preparation 12.

MS(m/e): 260 (M⁺); Calculated for $C_{12}H_{13}N_5O_2$: Theory: C, 55.59; H, 5.05; N, 27.01; Found: C, 55.87; H, 5.17; N, 26.92.

Preparation 14

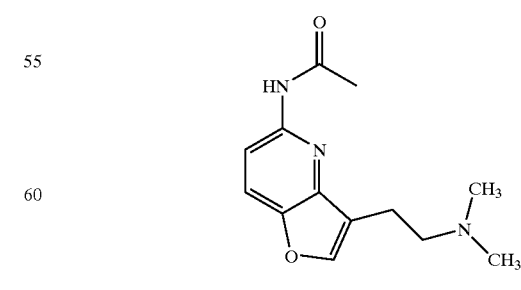

5-Acetylamino-3-[2-(N,N-dimethylamino)ethyl]furo[3,2-b]pyridine

To a solution of 5-acetylamino-3-(2-azidoethyl)furo[3,2-b]pyridine (1.65 g, 6.5 mmol) dissolved in ethanol (300 mL) was added 200 mg of 10% palladium on carbon. The mixture was hydrogenated at room temperature under 30 psi of hydrogen pressure for 2 h, filtered through celite, and concentrated in vacuo. The crude material was dissolved in methanol (180 mL), cooled to 0° C., and treated with sodium cyanoborohydride (0.41 g, 16.2 mmol), acetic acid (2.0 mL, 32.4 mmol), and formaldehyde (37 wt. % in water, 1.66 mL, 19.5 mmol). The reaction was warmed to room temperature and stirred overnight. The solvent was removed, and the solid residue was partitioned between 3:1 chloroform/isopropyl alcohol and water. The aqueous layer was adjusted to pH=14 with 1 N aqueous NaOH, extracted with chloroform, and the combined organics were washed with saturated aqueous NaCl, dried over $Na_2SO_4$, and concentrated. The residue was chromatographed on silica gel (0→20% 2 M $NH_3$-methanol/dichloromethane) to provide 1.26 g (79%) of the desired material. An analytical sample of the oxalate salt was prepared.

m.p.=168–170° C.; MS(m/e): 248 ($M^+$); Calculated for $C_{13}H_{17}N_3O_2 \cdot C_2H_2O_4$: Theory: C, 53.41; H, 5.68; N, 12.46; Found: C, 53.57; H, 5.91; N, 12.57.

Preparation 15

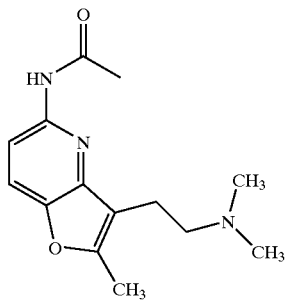

5-Acetylamino-3-[2-(N,N-dimethylamino)ethyl]-2-methylfuro[3,2-b]pyridine

The title compound was prepared from 5-acetylamino-3-(2-azidoethyl)-2-methylfuro[3,2-b]pyridine in the manner described in Preparation 14 in 83% isolated yield.

m.p.=138–139° C.; MS(m/e): 260 ($M^+$); Calculated for $C_{14}H_{19}N_3O_2$: Theory: C, 64.35; H, 7.33; N, 16.08; Found: C, 64.14; H, 7.09; N, 16.07.

Preparation 16

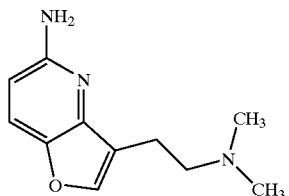

5-Amino-3-[2-(N,N-dimethylamino)ethyl]furo[3,2-b]pyridine

A solution of 5-acetylamino-3-[2-(N,N-dimethylamino)ethyl]furo[3,2-b]pyridine (1.26 g, 5.10 mmol) dissolved in 120 mL of 1 N aqueous HCl was heated at 70° C. for 3 h. The reaction was cooled to room temperature, basified to pH >12 with 5 N aqueous NaOH, and extracted with 3:1 chloroform/isopropyl alcohol. The combined organic extracts were washed with saturated aqueous NaCl, dried over $Na_2SO_4$, and concentrated. Chromatography (0→20% 2 M $NH_3$-methanol/dichloromethane) provided the desired material (85% yield) as white solid. A sample of the oxalate salt was prepared for analysis.

m.p.=122–124° C.; MS(m/e): 206 ($M^+$); Calculated for $C_{11}H_{15}N_3O \cdot C_2H_2O_4 \cdot 0.5\ CH_4O$: Theory: C, 52.08; H, 6.15; N, 13.50; Found: C, 52.03; H, 6.03; N, 13.51.

Preparation 17

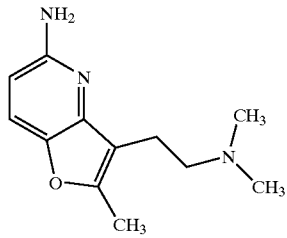

5-Amino-3-[2-(N,N-dimethylamino)ethyl]-2-methylfuro-[3,2-b]pyridine

The title compound was prepared from 5-acetylamino-3-[2-(N,N-dimethylamino)ethyl]-2-methylfuro[3,2-b]pyridine in the same manner as 5-amino-3-[2-(N,N-dimethylamino)ethyl]furo[3,2-b]pyridine, providing the title compound as an amorphous white solid (79%).

m.p.=103–104° C.; MS(m/e): 220 ($M^+$); Calculated for $C_{12}H_{17}N_3O$: Theory: C, 65.73; H, 7.81; N, 19.16; Found: C, 65.65; H, 7.84; N, 18.93.

EXAMPLE 1 & 2

5-Amido-3-2-(N,N-dimethylamino)ethyl]furo[3,2-b]pyridine and 5-Amido-3-[2-(N,N-dimethylamino)ethyl]-2-methylfuro[3,2-b]pyridine To a solution of the appropriate 5-aminofuro[3,2-b]pyridine prepared above (0.37 mmol) dissolved in 15 mL of pyridine was added the acid chloride (0.52 mmol). The reaction mixture was heated at 55° C. for 2 h, then concentrated in vacuo. The residue was partitioned between 3:1 chloroformn/isopropyl alcohol and 0.1 N aqueous NaOH. The aqueous layer was extracted with chloroform and the combined organics were washed with saturated aqueous NaCl, dried over $Na_2SO_4$, and concentrated. Chromatography (0→10% 2 M $NH_3$-methanol/dichloromethane) provided the title compound which was analyzed either as the free base or converted to the oxalate salt.

Examples 3–12 were prepared and isolated in the same manner as Examples 1–2.

EXAMPLE 3

3-[2-(N,N-Dimethylamino)ethyl]-5-propanoylaminofuro[3,2-b]pyridine Oxalate

The title compound was isolated in 83% yield as the oxalate salt.

m.p.=153–155° C.; Calculated for $C_{14}H_{19}N_3O_2 \cdot C_2H_2O_4 \cdot 0.5\ CH_4O$: Theory: C, 54.31; H, 6.17; N, 11.69; Found: C, 54.38; H, 6.19; N, 11.35.

EXAMPLE 4

5-Benzoylamino-3-[2-(N,N-dimethylamino)ethyl]furo[3,2-b]pyridine Oxalate

The title compound was isolated in 73% yield as the oxalate salt.

m.p.=65–66° C.; Calculated for $C_{18}H_{19}N_3O_2 \cdot C_2H_2O_4$: Theory: C, 60.14; H, 5.30; N, 10.52; Found: C, 60.39; H, 5.45; N, 10.46.

EXAMPLE 5

3-[2-(N,N-Dimethylamino)ethyl]-5-(4-fluorobenzoyl)aminofuro[3,2-b]pyridine Oxalate The title compound was isolated in 80% yield as the oxalate salt.

m.p.=124–126° C.; MS(m/e): 328 (M$^+$); Calculated for $C_{18}H_{18}FN_3O_2 \cdot C_2H_2O_4$: Theory: C, 57.55; H, 4.83; N, 10.07; Found: C, 57.85; H, 4.95; N, 10.15.

EXAMPLE 6

3-[2-(N,N-Dimethylamino) ethyl]-5-(2-thienoyl)aminofuro[3,2-b]pyridine Oxalate The title compound was isolated in 83% yield as the oxalate salt.

m.p.=68–69° C.; MS(m/e): 330 (M$^+$); Calculated for $C_{16}H_{17}N_3O_2S \cdot C_2H_2O_4$: Theory: C, 53.33; H, 4.72; N, 10.36; Found: C, 53.51; H, 4.64; N, 10.34.

EXAMPLE 7

5-(2,4-Difluorobenzoyl)amino-3-[2-(N,N-dimethylamino)ethyl]furo[3,2-b]pyridine Oxalate The title compound was isolated in 90% yield as the oxalate salt.

MS(m/e): 346 (M$^+$).

EXAMPLE 8

3-[2-(N,N-Dimethylamino)ethyl]-2-methyl-5-propanoylaminofuro[3,2-b]pyridine Oxalate The title compound was isolated in 80% yield as the oxalate salt.

m.p.=168–170° C.; MS(m/e): 276 (M$^+$); Calculated for $C_{14}H_{19}N_3O_2 \cdot C_2H_2O_4 \cdot 0.5\ CH_4O$: Theory: C, 55.11; H, 6.61; N, 11.02; Found: C, 55.31; H, 6.54; N, 10.81.

EXAMPLE 9

5-Benzoylamino-3-[2-(N,N-dimethylamino)ethyl]-2-methylfuro[3,2-b]pyridine

The title compound was isolated in 74% yield as the free base.

m.p.=119–120° C.; MS(m/e): 324 (M$^+$); Calculated for $C_{19}H_{21}N_3O_2$: Theory: C, 70.57; H, 6.55; N, 12.99; Found: C, 70.32; H, 6.81; N, 12.92.

EXAMPLE 10

3-[2-(N,N-Dimethylamino)ethyl]-5-(4-fluorobenzoyl)amino-2-methylfuro[3,2-b]pyridine Oxalate The title compound was isolated in 80% yield as the oxalate salt.

m.p.=136–138° C.; MS(m/e): 342 (M$^+$); Calculated for $C_{14}H_{19}N_3O_2 \cdot C_2H_2O_4 \cdot 0.25\ CH_4O$: Theory: C, 58.08; H, 5.28; N, 9.56; Found: C, 57.33; H, 5.05; N, 9.28.

EXAMPLE 11

3-[2-(N,N-Dimethylamino)ethyl]-2-methyl-5-(2 thienoyl)aminofuro[3,2-b]pyridine Oxalate The title compound was isolated in 90% yield as the oxalate salt.

m.p.=211–212° C.; MS(m/e): 330 (M$^+$); Calculated for $C_{17}H_{19}N_3O_2S \cdot C_2H_2O_4$: Theory: C, 54.41; H, 5.05; N, 10.02; Found: C, 54.65; H, 4.97; N, 10.06.

EXAMPLE 12

5-(2,4-Difluorobenzoyl)amino-3-[2-(N,N-dimethylamino)ethyl]-2-methylfuro[3,2-b]pyridine The title compound was isolated in 74% yield as the free base.

MS(m/e): 360 (M$^+$).

The type of formulation employed for the administration of the compounds employed in the methods of the present invention may be dictated by the particular compounds employed, the type of pharmacokinetic profile desired from the route of administration and the compound(s), and the state of the patient.

Formulations amenable to oral or injectable administration are prepared in a manner well known in the pharmaceutical art and comprise at least one active compound. See, e.g., *Remington's Pharmaceutical Sciences*, (16th ed. 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a compound of formula I.

FORMULATION EXAMPLE 1

Hard Gelatin Capsules

| Ingredient | Quantity (mg/capsule) |
| --- | --- |
| 2-methyl-3-(2-[N'-methyl-N'-s-butylamino]ethyl)-5-isobutyramide-furo[3,2-b]pyridine | 30.0 |
| Starch | 305.0 |
| Magnesium stearate | 5.0 |

The above ingredients are mixed and filled into hard gelatin capsules in 340 mg quantities.

FORMULATION EXAMPLE 2

Tablet

| Ingredient | Quantity (mg/tablet) |
| --- | --- |
| 2-methyl-3-(2-[N'-methyl-N'-(2-[pyridin-4-yl]-ethyl)amino]-ethyl)-5-(4-fluorobenzamide)furo-[3,2-b]pyridine malonate | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

Dry Powder Inhaler

| Ingredient | Weight % |
| --- | --- |
| 2-methyl-3-(2-[N'-methyl-N'-([2-aminobenzothiazol-5-yl]-methyl)amino]ethyl)-5-(4-fluorobenzamide)-furo[3,2-b]pyridine | 5 |
| Lactose | 95 |

The active ingredient is mixed with the lactose and the mixture is added to a dry powder inhaling appliance.

FORMULATION EXAMPLE 4

Tablet

| Ingredient | Quantity (mg/tablet) |
| --- | --- |
| 2-methyl-3-(2-[N'-methyl-N'-([thiazol-2-yl]methyl)amino]ethyl)-5-cycloheptanecarboxamidefuro-[3,2-b]pyridine | 30.0 |
| Starch | 45.0 |

-continued

| Ingredient | Quantity (mg/tablet) |
| --- | --- |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules

| Ingredient | Quantity (mg/capsule) |
| --- | --- |
| 2-methyl-3-(2-[N'-methyl-N'-(2-[1-isopropylpyrazol-4-yl]-ethyl)amino]ethyl)-5-butyramidefuro[3,2-b]pyridine | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories

| Ingredient | Amount |
| --- | --- |
| 3-(2-[N'-methyl-N'-([4-bromothien-2-yl]methyl)-amino]ethyl)-5-(4-fluoro-benzamide)furo[3,2-b]pyridine | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions

| Ingredient | Amount |
| --- | --- |
| 2-ethyl-3-(2-[N'-ethyl-N'-(2-(3-methylthiobenzofur-5-yl]ethyl)-amino]ethyl)-5-(pyridine-2-carboxamide)furo[3,2-b]pyridine; | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules

| Ingredient | Quantity (mg/capsule) |
| --- | --- |
| 2-propyl-3-(2-[N'-isopropyl-N'-(3-[isobenzofur-2-yl]propyl)amino]-ethyl)-5-(4-fluorobenzamide)-furo[3,2-b]pyridine | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

Intravenous Formulation

| Ingredient | Quantity |
| --- | --- |
| 2-methyl-3-(2-[N'-butyl-N'-([pyrrol-3-yl]methyl)amino]ethyl)-5-(4-fluorobenzamide)furo-[3,2-b]pyridine | 250.0 mg |
| Isotonic saline | 1000 ml |

FORMULATION EXAMPLE 10

Topical Formulation

| Ingredient | Quantity |
| --- | --- |
| 2-methyl-3-(2-[N'-methyl-N'-([5-cyanoimidazol-2-yl]methyl)amino]-ethyl)-5-acetamidefuro[3,2-b]pyridine | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or Buccal Tablets

| Ingredient | Quantity (mg/tablet) |
| --- | --- |
| 2-methyl-3-(2-[N'-methyl-N'-([isoquinolin-7-yl]methyl)amino]ethyl)-5-cyclobutanecarboxamidefuro-[3,2-b]pyridine | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of formula I:

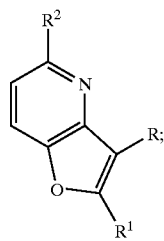

I and pharmaceutical acid addition salts thereof, where;

R is

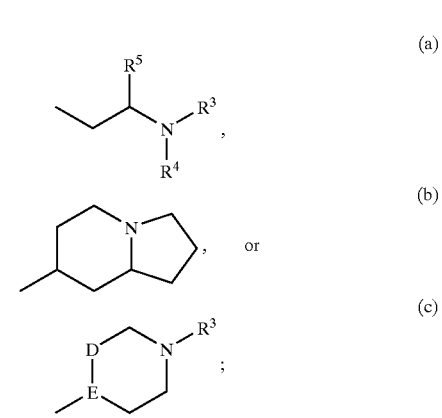

E—D is C=CH or CH—CH$_2$;
R$^1$ is hydrogen or C$_1$–C$_4$ alkyl;
R$^2$ is hydrogen, halo, hydroxy, —NR$^3$R$^4$, —SR$^3$, —C(O)R$^3$, —C(O)NR$^3$R$^4$, —NR$^3$SO$_2$R$^5$, —NHC(Q)NR$^3$R$^4$, —NHC(O)OR$^3$, or —NR$^3$C(O)R$^5$;
R$^3$, R$^4$, and R$^5$ are independently hydrogen, C$_1$–C$_4$ alkyl, C$_2$–C$_6$ alkenyl, C$_2$–C$_6$ alkynyl, or —(CH$_2$)$_n$ aryl; or R$^3$ and R$^4$ combine, together with the nitrogen to which they are attached, form a pyrrolidine, piperidine, piperazine, 4-substituted piperazine, morpholine, or thiomorpholine ring;
n is 0, 1, 2, 3, 4, 5, or 6; and
Q is O or S.

2. The compound of claim 1 where R is moiety (a).
3. The compound of claim 2 where R$^3$ is C$_1$–C$_4$ alkyl.
4. The compound of claim 2 where R$^6$ is C$_1$–C$_4$ alkyl.
5. The compound of claim 2 where R$^1$ is methyl.
6. The compound of claim 4 where R$^3$ is methyl and R$^4$ is methyl.
7. The compound of claim 1 where R is moiety (c).
8. The compound of claim 7 where R$^3$ is C$_1$–C$_4$ alkyl.
9. The compound of claim 8 where R$^3$ is methyl.
10. The compound of claim 8 where R$^2$ is —NHC(O)R$^5$.
11. The compound of claim 9 where R$^2$ is —NHC(O)R$^5$.
12. A pharmaceutical formulation comprising a compound of claim 1 and a pharmaceutical carrier, diluent, or excipient.
13. A pharmaceutical formulation comprising a compound of claim 7 and a pharmaceutical carrier, diluent, or excipient.
14. A pharmaceutical formulation comprising a compound of claim 11 and a pharmaceutical carrier, diluent, or excipient.
15. A method for treating migraine in a mammal comprising administering to a mammal in need of such treatment an effective amount of a compound of claim 1, or a pharmaceutical acid addition salt thereof.
16. A method for treating migraine in a mammal comprising administering to a mammal in need of such treatment an effective amount of a compound of claim 2, or a pharmaceutical acid addition salt thereof.
17. A method for treating migraine in a mammal comprising administering to a mammal in need of such treatment an effective amount of a compound of claim 7, or a pharmaceutical acid addition salt thereof.
18. A method for treating migraine in a mammal comprising administering to a mammal in need of such treatment an effective amount of a compound of claim 11 or a pharmaceutical acid addition salt thereof.

* * * * *

UNITED STATES PATENT AND TRADEMARK OFFICE
CERTIFICATE OF CORRECTION

PATENT NO.   : 6,696,439 B1
DATED        : February 24, 2004
INVENTOR(S)  : Filla et al.

It is certified that error appears in the above-identified patent and that said Letters Patent is hereby corrected as shown below:

Column 34,
Line 33, reads "…where $R^6$ is;" should read -- …where $R^4$ is… --

Signed and Sealed this

Twenty-second Day of March, 2005

JON W. DUDAS
*Director of the United States Patent and Trademark Office*